(12) United States Patent
Akbar et al.

(10) Patent No.: US 10,555,784 B2
(45) Date of Patent: Feb. 11, 2020

(54) ROBOTIC GUIDE FOR BRAIN BIOPSY

(71) Applicant: Parseh Intelligent Surgical System, Tehran (IR)

(72) Inventors: Mohammad Akbar, Tehran (IR); Seyed Mohammad Javad Mortazavi ashkezari, Tehran (IR); Javad Hasani bidgoli, Tehran (IR); Amirhossein Ahmadian, Tehran (IR); Mohammad Jalal Sadeghi, Tehran (IR); Alireza Ahmadian, Tehran (IR); Farzam Farahmand, Tehran (IR); Saeed Sarkar, Tehran (IR)

( * ) Notice: Subject to any disclaimer, the term of this patent is extended or adjusted under 35 U.S.C. 154(b) by 243 days.

(21) Appl. No.: 15/829,791

(22) Filed: Dec. 1, 2017

(65) Prior Publication Data
US 2018/0085177 A1    Mar. 29, 2018

Related U.S. Application Data

(60) Provisional application No. 62/429,766, filed on Dec. 3, 2016.

(51) Int. Cl.
*A61B 34/30* (2016.01)
*A61B 10/02* (2006.01)
(Continued)

(52) U.S. Cl.
CPC .............. *A61B 34/30* (2016.02); *A61B 10/02* (2013.01); *A61B 34/35* (2016.02); *A61B 34/37* (2016.02);
(Continued)

(58) Field of Classification Search
CPC ......... A61B 34/30; A61B 34/35; A61B 34/37; A61B 34/70; A61B 10/02; A61B 2090/103; A61B 2034/302; A61B 2010/0208
See application file for complete search history.

(56) References Cited

U.S. PATENT DOCUMENTS

| | | | |
|---|---|---|---|
| 7,691,098 B2 * | 4/2010 | Wallace | A61B 34/71 606/1 |
| 7,822,466 B2 | 10/2010 | Stoianovici et al. | |

(Continued)

FOREIGN PATENT DOCUMENTS

| | | |
|---|---|---|
| CN | 2712301 Y | 7/2005 |
| CN | 104983467 A | 10/2015 |
| DE | 102011081420 A | 8/2012 |

OTHER PUBLICATIONS

Paul B. McBeth, Robotics in neurosurgery, The American Journal of Surgery, Oct. 2004, vol. 188, 68-S-75S.
(Continued)

*Primary Examiner* — Julian W Woo (57) ABSTRACT

Various robotic guides for a biopsy surgical tool are disclosed, of which one includes a main shaft, an end-effector mounted on a distal end of the main shaft, a roll/yaw actuating mechanism, a translational actuating mechanism, and a pitch actuating mechanism. Optionally, the roll/yaw actuating mechanism includes a first actuating mechanism and a second actuating mechanism. Roll movement or yaw movement of the main shaft is effectuated by combination of movements of the first actuating mechanism and the second actuating mechanism.

9 Claims, 9 Drawing Sheets

(51) Int. Cl.
*A61B 34/37* (2016.01)
*A61B 34/00* (2016.01)
*A61B 34/35* (2016.01)
*A61B 90/10* (2016.01)

(52) U.S. Cl.
CPC ...... *A61B 34/70* (2016.02); *A61B 2010/0208* (2013.01); *A61B 2034/302* (2016.02); *A61B 2090/103* (2016.02)

(56) References Cited

U.S. PATENT DOCUMENTS

| | | | |
|---|---|---|---|
| 8,911,428 B2 * | 12/2014 | Cooper | A61B 17/00234 606/1 |
| 9,314,305 B2 | 4/2016 | Jenkins et al. | |
| 9,839,481 B2 * | 12/2017 | Blumenkranz | A61B 17/2909 |
| 2018/0049798 A1 * | 2/2018 | Shelton, IV | A61B 34/30 |

OTHER PUBLICATIONS

Derya Yakar, Feasibility of a Pneumatically Actuated MR-compatible Robot for Transrectal Prostate Biopsy Guidance, Journal of radiology, Jul. 2011, vol. 260, Issue 1, 241-247.

Michael H. Loser, A New Robotic System for Visually Controlled Percutaneous Interventions under CT Fluoroscopy, International Conference on Medical Image Computing and Computer-Assisted Intervention, 2000, vol. 1935, 887-896.

Ken Masamune, Development of an MRI-Compatible Needle Insertion Manipulator for Stereotactic Neurosurgery, Journal of Image Guided Surgery, Jan. 6, 2010, Issue 1, 242-248.

Ozkan Bebek, Design of a Parallel Robot for Needle Based Interventions on Small Animals, IEEE Transactions on Mechatronics, Aug. 18, 2011, vol. 18, issue 1, 62-73.

Yik San Kwoh, A Robot with Improved Absolute Positioning Accuracy for CT Guided Stereotactic Brain Surgery, IEEE Transactions on Biomedical Engineering, Feb. 1988, vol. 35, No. 2, 153-160.

Riccardo Muradore, Development of a Cognitive Robotic System for Simple Surgical Tasks, Int J Adv Robot Syst, 2015, vol. 12, Issue 37, pp. 1-20.

Sang-Eun Song, Development of a Pneumatic Robot for MRI-guided Transperineal Prostate Biopsy and Brachytherapy: New Approaches, IEEE International Conference on Robotics and Automation, May 3-8, 2010, pp. 2580-2585.

* cited by examiner

ROBOTIC GUIDE FOR BRAIN BIOPSY

CROSS-REFERENCE TO RELATED APPLICATION

This application claims the benefit of priority from U.S. Provisional Patent Application Ser. No. 62/429,766, filed on Dec. 3, 2016, and entitled "ROBOTIC BRAIN BIOPSY SYSTEM" which is incorporated herein by reference in its entirety.

TECHNICAL FIELD

The present disclosure generally relates to biopsy systems and particularly to a robotic guide that provide a number of degrees of freedom and is utilized in biopsy systems.

BACKGROUND

Brain surgeries are becoming acceptable therapeutic and diagnostic modality in the neurosurgical treatment of patients suffering, for example, from chronic pain, Parkinson's disease, seizure, and other medical conditions. Among brain surgeries, brain biopsy is a common diagnostic surgery. A brain biopsy is the removal of a small piece of a brain tissue for the diagnosis of the brain abnormalities. A brain biopsy is used to diagnose Alzheimer's disease, tumors, infections, inflammations, and other brain disorders. By examining the tissue sample under a microscope, the biopsy sample provides doctors with the information necessary for diagnosis and treatment. The biopsy surgeries are categorized based on the technique and the needle size used for tissue extraction. A stereotactic biopsy, otherwise known as a core biopsy, is one of the least invasive types of biopsies. In a stereotactic biopsy procedure, 3-D imaging technology, as well as data from CT (Computer Tomography) and MRI (Magnetic Resonance Imaging) scans are utilized to examine a tissue sample from a brain. Images that are taken in at least two planes may be used to pinpoint a tissue location (hereinafter target), such as a tumor or microcalcifications in a breast. The pinpointed location may be used to help guide the tissue removal procedure. In a stereotactic biopsy procedure, the underlying principle of parallax may be utilized to determine the depth or "Z-dimension" of the target.

During the above-described stereotactic biopsies, as various other biopsy techniques, visual information may be simultaneously provided for the surgeon in real-time. An example of such visual information can include detailed information of the 3D path the surgeon must navigate to perform the biopsy, as well as real-time information tracking the surgical instrument. Providing the visual information utilization and real-time tracking of instruments during the surgical procedures can help enhance the precision and quality of the surgeries.

Notwithstanding the above-described providing of information to the surgeon, in stereotactic biopsy procedures, in guiding the biopsy needle to the target, actions of movement must be performed directly by the surgeon. Requiring substantial actions from the surgeon makes the biopsy procedure dependent on the surgeon's proficiency and dexterity. In addition, when an imaging equipment such as a CT scanner is used, some harmful rays may be spread out to the surgery room and consequently, in order to protect the surgeon from harmful rays, a protection mechanism may be used. The protection mechanism may substantially increase the biopsy procedure's cost, and also may affect the precision and quality of the biopsy procedure.

Therefore, there is a need in the art for stereotactic biopsy systems and devices in which the stereotactic biopsy procedures are accomplished more accurately without requiring direct actions taken by the surgeon.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

To achieve more accurate and higher quality biopsies, a robotic guide may be utilized to provide a path for biopsy needle. Utilizing a robotic guide in a biopsy procedure may obviate necessity of direct actions from the surgery and also may provide certain cost advantages relative to manual biopsy procedure. by using visual information and surgical navigation systems.

Disclosed apparatuses include a robotic guide for a biopsy surgical tool, and in an aspect, robotic guide can include a main shaft, supported and rotatable about a main shaft axis, an end-effector, connected by movably to a distal end of the main shaft in a configuration rotatable about a pitch axis, and a roll/yaw actuating mechanism. In one implementation, the roll/yaw actuating mechanism can include a first actuating mechanism, including a pinion mounted on a bottom of the main shaft, a bottom gear meshedly engaged with a bottom portion of the pinion, and rotatable about a yaw axis, and a first motor, coupled though a first coupling to the bottom gear, configured to convert rotation of the first motor to a rotation of the bottom gear. In one implementation, the roll/yaw actuating mechanism can also include a second actuating mechanism, including a top gear meshedly engaged with a top portion of the pinion, a second motor, coupled though a second coupling to the bottom gear, configured to convert rotation of the second motor to a rotation of the top gear, wherein rotational movements of the first motor and the second motor that convert to rotation of the top gear and the bottom gear in a similar direction lock the pinion from rotating, and urge movement of the main shaft that moves its distal end and the end effector in a yaw direction around the yaw axis, and rotational movements of the first motor and the second motor convert to rotation of the top gear and the bottom gear in mutually opposite directions rotate the main shaft about a roll axis, via the pinion. In an implementation, the robotic guide can also include a translational actuating mechanism, including a third motor, a middle hollow rod, coupled to the third motor in a configuration wherein a rotation by the third motor urges a rotation of the middle hollow rod, the middle hollow rod including a first externally threaded section provided on an exterior surface thereof, and a first internally threaded section provided on an interior surface of the main shaft, the first internally threaded section being meshed with the first externally threaded section of the middle hollow rod such that a rotational movement of the middle hollow rod urges a linear movement of the main shaft. In an implementation, the robotic guide can also include a pitch actuating mechanism, including a slider-crank mechanism, movably supported by the main shaft for movement of a crank end in a direction of the roll axis, the crank end being coupled to the end-effector in a configuration wherein movement of the crank end in the direction of the roll axis urges a pitch rotation of the end-effector.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

Disclosure includes another implementation of a robotic guide for a biopsy surgical tool. In this implementation, the robotic guide may include a main shaft, an end-effector mounted on a distal end of the main shaft, a roll/yaw actuating mechanism, a translational actuating mechanism, and a pitch actuating mechanism. In some implementations, the roll/yaw actuating mechanism may include a first actuating mechanism and a second actuating mechanism. The first actuating mechanism may include a first screw/nut mechanism in which a first nut mounted on a first screw that is coupled to a first motor. The first screw/nut mechanism may be configured to convert a rotational movement of the first motor to a linear movement of the first nut along a first axis. In one aspect of the present disclosure, a first plurality of balls may be movably disposed within a first curved guiding path such that the first nut is engaged between the first plurality of balls and consequently the linear movement of the first nut along the first axis urges movement of the first plurality of balls along the first curved guiding path. In another implementation, two extended parts of a bottom reduced bevel gear may be engaged with the first plurality of balls such that the movement of the first plurality of balls along the first curved guiding path convert the linear movement of the first nut along the first axis to rotational movement of the bottom reduced bevel gear around a central axis of the bottom reduced bevel gear. In some other implementations, the second actuating mechanism may include a second screw/nut mechanism in which a second nut mounted on a second screw that is coupled to a second motor. The second screw/nut mechanism may be configured to convert a rotational movement of the second motor to a linear movement of the second nut along a second axis. In one aspect of the present disclosure, a second plurality of balls may be movably disposed within a second curved guiding path such that the second nut is engaged between the second plurality of balls and consequently the linear movement of the second nut along the second axis urges movement of the second plurality of balls along the second curved guiding path. In another implementation, two extended parts of a top reduced bevel gear may be engaged with the second plurality of balls such that the movement of the second plurality of balls along the second curved guiding path convert the linear movement of the second nut along the second axis to rotational movement of the top reduced bevel gear around a central axis of the top reduced bevel gear. It could be understood that responsive to rotational movements of the first motor and the second motor in a similar direction, the main shaft rotates about the central axis and responsive to rotational movements of the first motor and the second motor in opposite directions, the main shaft rolls about a longitudinal axis of the main shaft.

In one aspect of the present disclosure, the translational actuating mechanism may include a third motor coupled with a middle hollow rod. The middle hollow rod may be in a threaded engagement with the main shaft such that the rotational movement of the middle hollow rod urges the linear movement of the main shaft. The pitch actuating mechanism may further include a fourth motor, a first solid rod that is coupled to the fourth motor, and a first hollow shaft that is rotationally coupled to the first solid rod. In some other implementations, the pitch actuating mechanism may include a second solid rod that is disposed slidably from a proximal end thereof in the first hollow shaft such that the rotational movement of the first hollow shaft urges the synchronous rotation of the second solid rod. The second solid rod may also have an externally threaded section at a distal end thereof that is meshed with the second internally threaded section of half-hollow rod such that the rotation of the second solid rod urges the linear movement of the half-hollow rod.

In one implementation, the end-effector may be mounted on a distal end of the main shaft such that the end-effector moves/rotates synchronously with the main shaft during yaw motion, roll motion and translational motion of the main shaft. Furthermore, the end-effector may be connected with a pin to a distal end of the half-hollow rod and consequently, responsive to the linear motion of the half-hollow rod, the end-effector tilts about the longitudinal axis of the main shaft through a slider-crank mechanism.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

As will be discussed herein, systems and methods directed to stereotactic biopsy systems that utilize a robotic surgical system with 7 degrees of freedom (DOFs) are disclosed. As noted above, in a stereotactic biopsy system, a surgical navigation technology simultaneously provides some visual information for the surgeon in real-time in order to analyze and control patient's conditions. Using a robotic surgical system in surgical navigation technology can facilitate utilizing of visual information and real-time tracking of an instrument during a stereotactic biopsy procedure. In some cases, the robotic surgical system in a stereotactic biopsy system may support 7 DOFs to simulate human arm behavior. This feature allows a surgeon to have substantially total control and maneuverability for securing the robotic surgical system to the patient's skull.

The robotic surgical systems in biopsy surgeries are generally integrated with a robotic guide which secures a path for a biopsy needle. In some implementations, the robotic guide may include an end-effector. The term "end-effector," as used herein, generally refers to a particular end linkage or segment that, depending on the robot's design, can securely grip, transport, orient, or otherwise release a workpiece or a surgical tool. The end-effector in a brain biopsy surgery generally includes a sheath defining a passage for the biopsy needle. The use of an integrated and exclusively designed robotic surgical system, which provides a path for a biopsy needle, may enhance the precision and quality of the biopsy surgery and furthermore, the use of integrated and exclusively designed robotic surgical system may reduce the dependency of biopsy surgery quality to the surgeon's dexterity.

The robotic surgical system of the present disclosure may include a control section and a robotic section. In some implementations, the robotic section of the stereotactic biopsy system may be configured to provide a number of DOFs and the control section of the stereotactic biopsy system may be configured to control the movements of the robotic section utilizing the DOFs.

In some implementations, the robotic section can include a passive segment and an active segment. The passive segment of the robotic surgical system can be configured to provide a number of passive DOFs to the robotic surgical system. Utilizing the passive DOFs, the passive segment of the robotic surgical system may facilitate the positioning of the robotic section in a work-space of the biopsy surgery near a patient's head by a surgeon. The passive segment of the surgical robotic system can be mounted, according to one aspect, on any fixed rigid appliance present in a surgery room. For example, in one implementation, the passive segment of the robotic surgical system can be mounted on a Mayfield surgical table and/or a side rail of the surgical table.

On the other hand, the active segment of the robotic surgical system may be able to provide 4 DOFs to the robotic surgical system. For purposes of reference, it should be understood that 4 DOFs are the minimum required DOFs to secure an end-effector of the robotic surgical system, such as a brain biopsy needle guide in an appropriate position and orientation for a biopsy procedure. However, in some implementations, the active segment of the robotic surgical system may include additional DOFs. For example, in one implementation, the active segment of the robotic surgical system allows for fine positioning of the end-effector of the robotic surgical system with respect to the target. Implementations according to disclosed aspect can provide certain cost and compactness advantages over existing systems.

Figure 1:
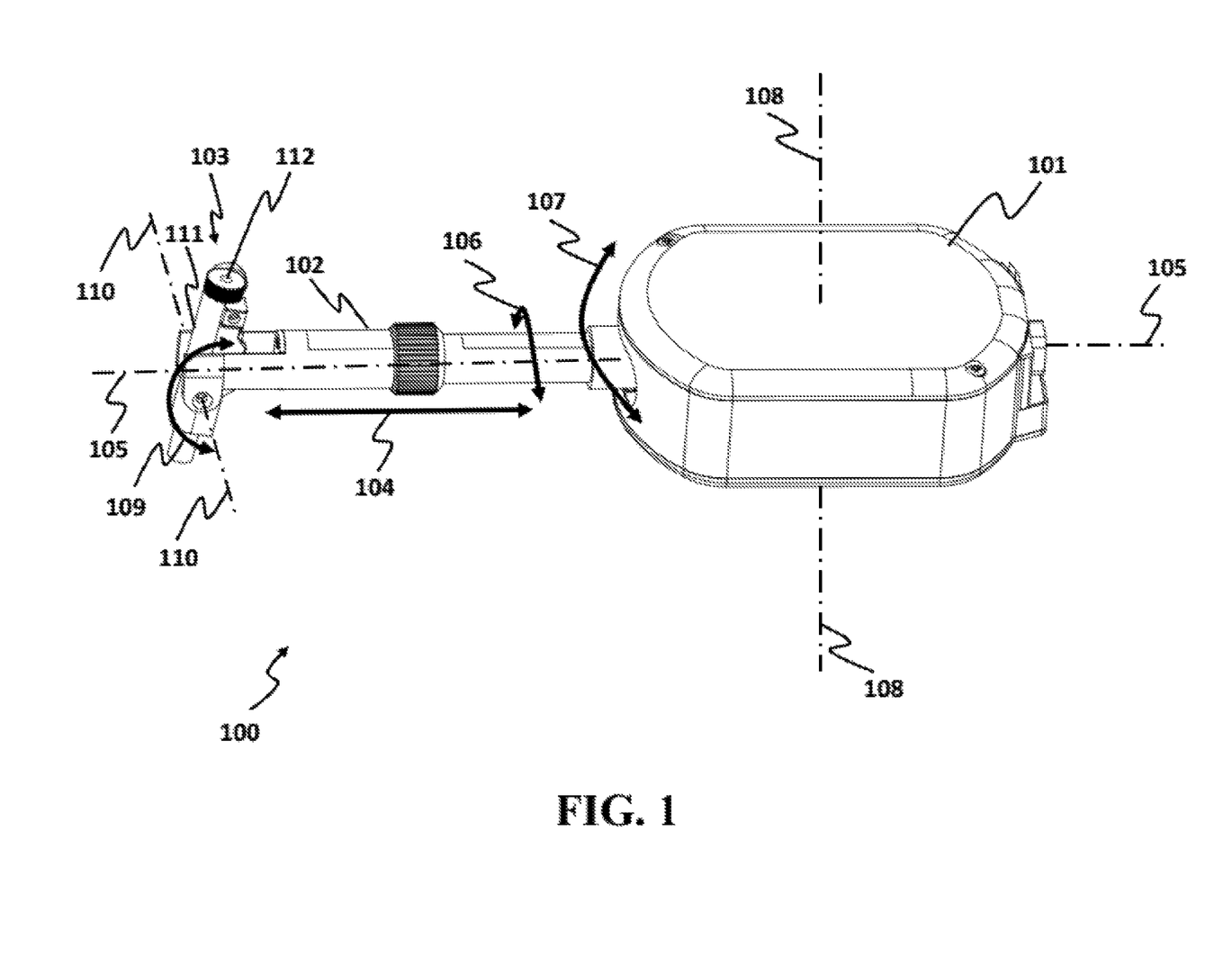
FIG. 1 illustrates an implementation of a robotic guide used as the active segment of a robotic brain biopsy system.

FIG. 1 shows a robotic guide 100 that can be utilized as the active segment of the robotic surgical system of a brain biopsy system. The robotic guide 100 can include an actuator assembly 101, a main shaft 102, and an end-effector 103. The actuator assembly 101 may include some actuating motors and gears, or pulleys, or both, that are configured to actuate DOFs of the robotic guide 100. The end-effector 103 can be mounted or otherwise attached to a distal end of the main shaft 102. The main shaft 102 is further configured to help provide a number of DOFs to the robotic guide 100. In one implementation, the end-effector 103 may include a sheath 111 defining a passage 112 for a biopsy needle (not explicitly shown in FIG. 1). In some implementations, the robotic guide 100 can include one translational degree of freedom 104 that allows for moving, e.g., extending and retracting, the main shaft 102 along a roll axis 105 that can be the same as a longitudinal axis of the main shaft 102. The robotic guide 100 can further include three rotational DOFs: a first rotational degree of freedom 106 that allows for rotating the main shaft 102 about the roll axis 105, a second rotational degree of freedom 107 that allows for rotating the main shaft 102 about a yaw axis 108, and a third rotational degree of freedom 109 that allows for rotating the end-effector 103 about a pitch axis 110. In other implementations, the robotic guide 100 may have additional DOFs.

Figure 2:
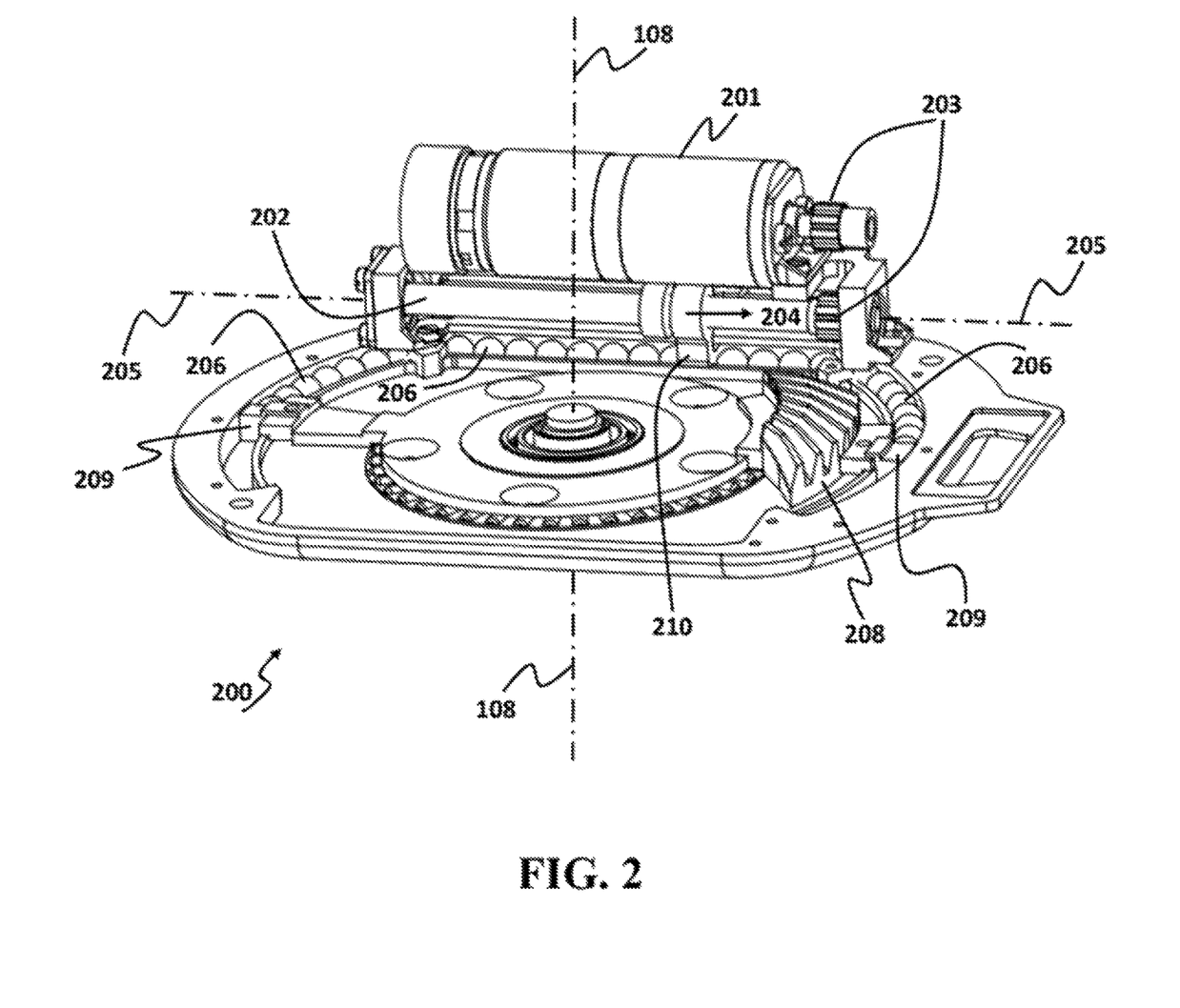
FIG. 2 illustrates a detailed perspective view of a bottom half of one example implementation of an actuator, which can be associated with various exemplary robotic guides in accordance with one or more aspects of the present disclosure.
Figure 3:
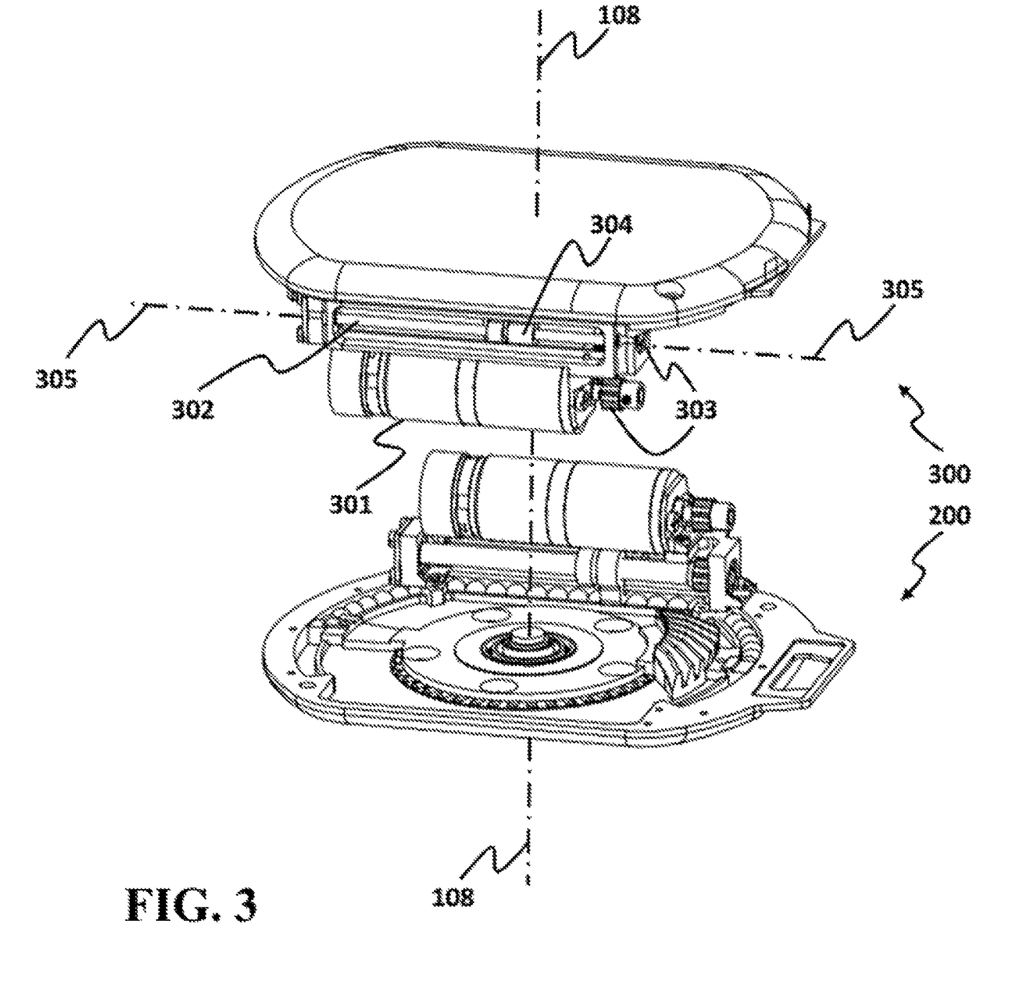
FIG. 3 illustrates an exploded view of a bottom half of one example implementation of an actuator, which can be associated with various exemplary robotic guides in accordance with one or more aspects of the present disclosure.
Figure 4:
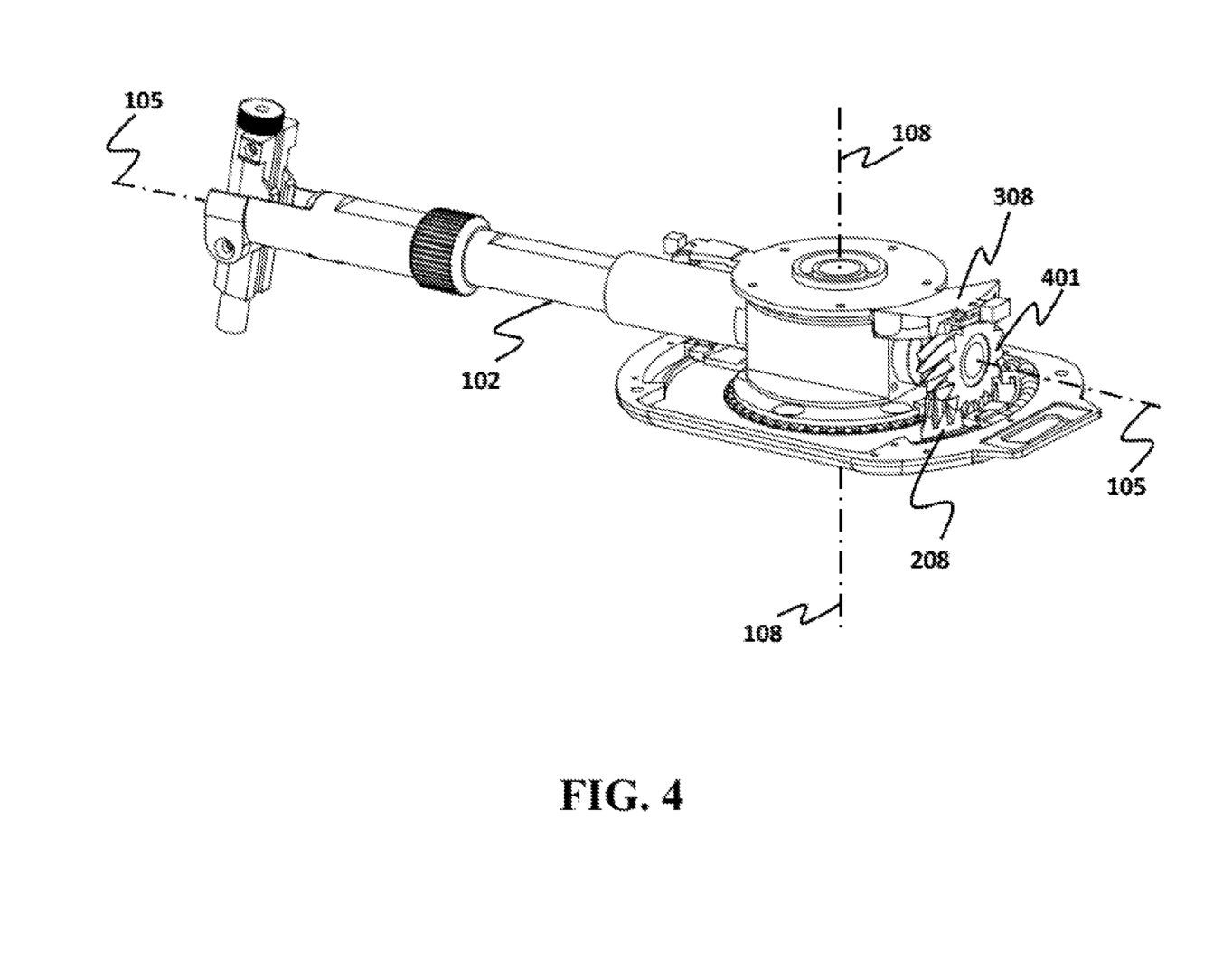
FIG. 4 illustrates a detailed perspective view of a structural aspect of an example implementation of the robotic guide that provides yaw and roll as degrees of freedom implementation, for one or more robotic guides according to aspects of the present disclosure.

For purposes of reference, FIGS. 2-4 provide an overview of various components and features in one implementation of the robotic guide 100 that, in combination, can provide the first rotational degree of freedom 106 and the second rotational degree of freedom 107.

FIG. 2 illustrates a perspective view of a bottom half 200 of the actuator assembly 101. As shown in FIG. 2, in one implementation, the bottom half 200 may include a first motor 201 coupled to a first nut/screw mechanism 202 via a first belt/pulley mechanism 203 (belt of the first belt/pulley mechanism 203 is not shown in FIG. 2), though in some other cases the first motor 201 is coupled to the first nut/screw mechanism 202 via other mechanisms, for example, a gear mechanism. Rotation of the first motor 201 may cause the translational movement of a first nut 204 along a first axis 205. In some implementations, the first nut 204 can include a first extended part 210 placed or otherwise engaged between a first plurality of balls 206. The engagement can be such that forward and reverse translational movement of the first nut 204 can urge corresponding forward and backward movements of the first plurality of balls 206 along a first curved guiding path 207. In some implementations, the first plurality of balls 206 may be confined between two extended parts 209 of a bottom reduced bevel gear 208. Consequently, the forward or backward movements of the first plurality of balls 206 along the first curved guiding path 207 can urge the bottom reduced bevel gear 208 to rotate about the gear 208 axis, which can be the yaw axis 108. The bottom reduced bevel gear 208 is termed "reduced" because its gear structure includes a multi-tooth segment or section of a bevel gear, as opposed to a complete ring-type bevel gear.

FIG. 3 illustrates an exploded view of the bottom half 200 of the actuator assembly 101 and a top half 300 of the actuator assembly 101. In some implementations, the top half 300 can be similar to the bottom half 200 of the actuator assembly 101 described in reference to FIG. 2. In other implementations, some components or aspects may be changed.

As shown in FIG. 3, in one implementation, the top half 300 can include a second motor 301 that may be substantially similar to the first motor 201 of FIG. 2 coupled to a second nut/screw mechanism 302. The second nut/screw mechanism 302 can be, but is not necessarily, substantially similar to the first nut/screw mechanism 202 of FIG. 2. The coupling of the second motor 301 to the second nut/screw mechanism 302 can be via a second belt/pulley mechanism 303 which can be, but is not necessarily, substantially similar to the first belt/pulley mechanism 203 of FIG. 2. In alternative implementations, the second motor 301 can be coupled to the second nut/screw mechanism 302 via other mechanisms, for example, a gear mechanism. The coupling can be configured such that rotation of the second motor 301 urges a translational movement of a second nut 304 along a second axis 305. In an aspect, the second axis 305 can be parallel the first axis first axis 205. In some implementations, the second nut 304 can include a second extended part (obscured from view in FIG. 3) that can be placed or otherwise engaged between a second plurality of balls (obscured from view in FIG. 3) and consequently translational movement of the second nut 304 can urge the back and forth movement of the second plurality of balls along a second curved guiding path. In some implementations, the second plurality of balls can be confined between two extended parts of a top reduced bevel gear (labeled "308" in FIG. 4, obscured from view in FIG. 3), in a configuration such that movements of a second plurality of balls 306 along the second curved guiding path can urge a rotation of the top reduced bevel gear about its rotational axis (not visible in FIG. 3).

FIG. 4 depicts a perspective view of the robotic guide 100. According to FIG. 4, a pinion 401, which is mounted on a proximal end of the main shaft 102, may be interposed meshably between the bottom reduced bevel gear 208 and the top reduced bevel gear 308. As Illustrated in FIG. 4, the bottom reduced bevel gear 208 and the top reduced bevel gear 308 can be aligned such that the rotational axis of each is co-linear with the yaw axis 108. The top reduced bevel gear 308 can have a meshed engagement with a top region (visible in FIG. 4 but not separately labeled) of the pinion 401, and the bottom reduced bevel gear 208 can have a meshed engagement with a bottom (visible in FIG. 4 but not separately labeled) of the pinion 401. With the further reference to FIG. 4, it can be understood that responsive to rotational movements of the bottom reduced bevel gear 208 and the top reduced bevel gear 308 in similar directions with similar rotational speeds, the main shaft 102 may rotate about the yaw axis 108 without any surplus rotation about the roll axis 105. Likewise, it can be understood that responsive to rotational movements of the bottom reduced bevel gear 208 and the top reduced bevel gear 308 in opposite directions with similar rotational speeds, the main shaft 102 may rotate about the roll axis 105 without causing movement of the main shaft 102 that would rotate the end-effector 103 about the yaw axis 108.

In addition, it will be understood that rotation of the main shaft 102 about the roll axis 105, simultaneous with movement of the main shaft 102, and hence the end effector 103, about the yaw axis 108 can be accomplished by adjusting relative speed and relative direction of the rotational movements of the bottom reduced bevel gear 208 and the top reduced bevel gear 308.

It will be understood that the illustrated first nut/screw mechanism 202 and the second nut/screw mechanism 302 can provide a self-locking mechanism against external forces urging movement relative to the first rotational degree of freedom 106 and against urging movement relative to the second rotational degree of freedom 107. More specifically, the first nut/screw mechanism 202 prevents externally-urged linear movement of the first nut 204 in the direction of the first axis 205, and the second nut/screw mechanism 302 prevents externally-urged linear movement of the second nut 304 in the direction of second axis 305. In combination, the first nut/screw mechanism 202 and the second nut/screw mechanism 302 can therefore secure the main shaft 102 against external forces and torques that may otherwise cause the main shaft 102 to rotate in either direction of the first rotational degree of freedom 106, or cause movement the main shaft 102 in either direction of the second rotational degree of freedom 107.

Figure 5A:
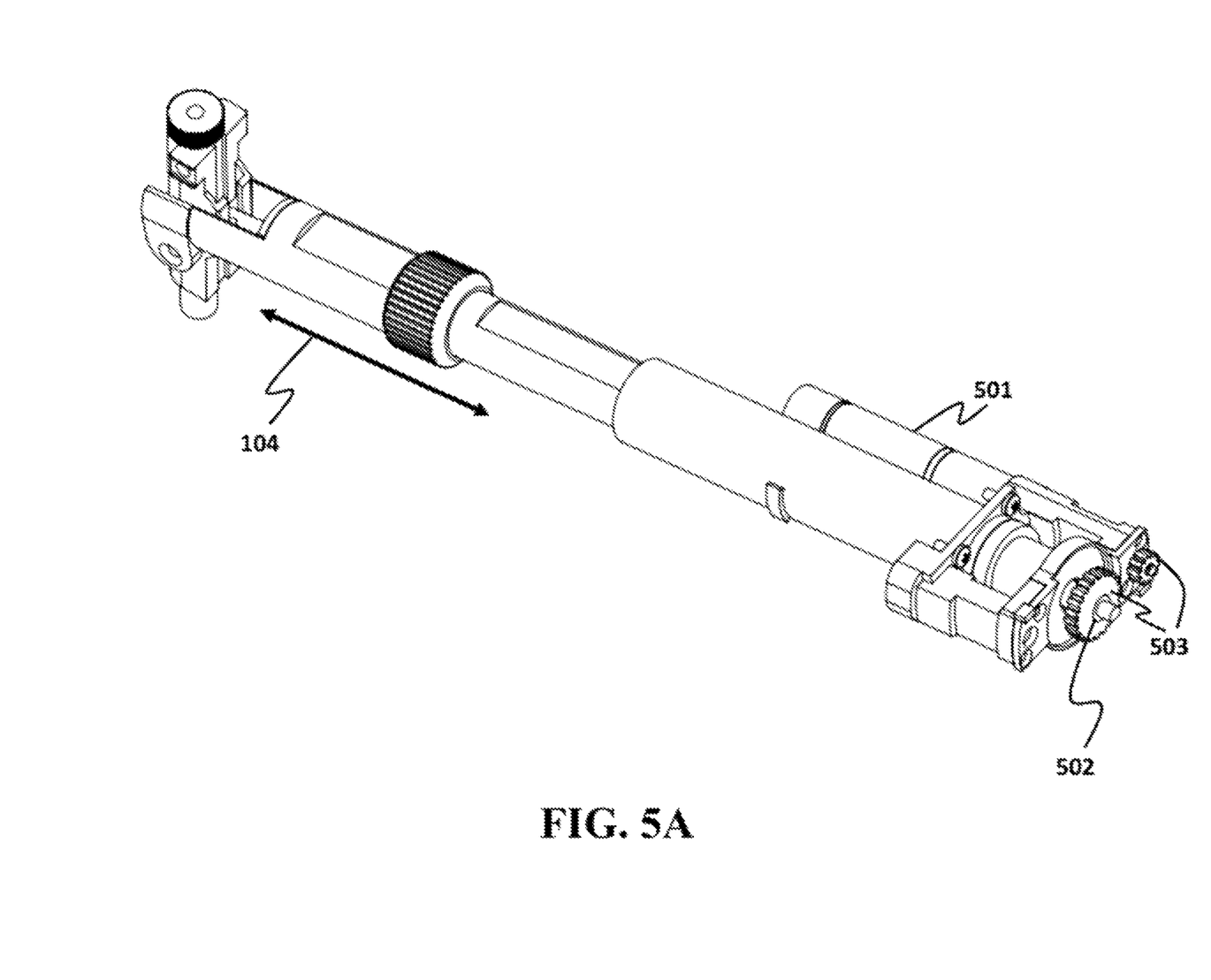
FIG. 5A illustrates a detailed perspective view of an example implementation of a structural aspect of the robotic guide that can provide, for example, a translational degree of freedom.
Figure 5B:
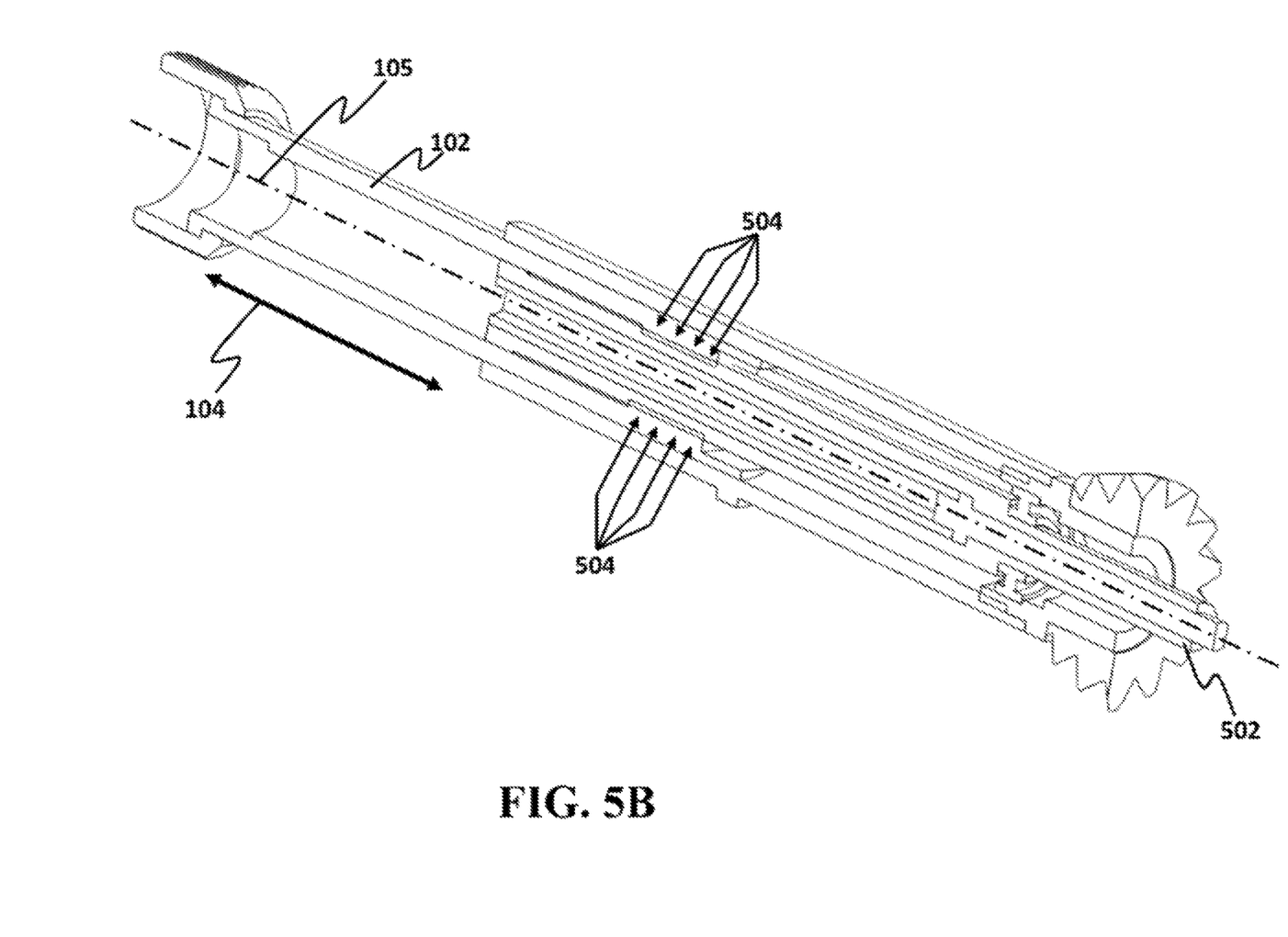
FIG. 5B illustrates a detailed sectional view of an implementation of the robotic guide's components included in providing a translational degree of freedom.

For purposes of reference, FIGS. 5A and 5B provide an additional view of various components and features of the robotic guide 100 that are configured together to provide the translational degree of freedom 104 for the robotic guide 100. Referring to FIG. 5A, in some implementations, the disclosed robotic guide 100 can include a third motor 501 coupled to a middle hollow rod 502 via a third belt/pulley mechanism 503 (belt of the third belt/pulley mechanism 503 is not shown in FIG. 5A). In alternative implementations, the third motor 501 can be coupled to the middle hollow rod 502 via other mechanisms, for example, a gear mechanism. FIG. 5B shows a sectional view of the robotic guide 100, according to one implementation of the present disclosure. In an aspect, the main shaft 102 can include an internal threaded section 504, and middle hollow rod 502 can include a threaded outer section (visible in FIG. 5B but not separately labeled) that can be in a threaded engagement with the threaded section 504 of the main shaft 102. Due to the threaded engagement between the main shaft 102 and the middle hollow rod 502 at the threaded section 504 of an interior surface of the main shaft 102, the main shaft 102 can act as a nut for the middle hollow rod 502. Accordingly, in response to a rotation of the middle hollow rod 502, the main shaft 102 may be urged and moved linearly in the direction of the roll axis 105, thereby providing the translational degree of freedom 104 for the robotic guide 100.

The threaded engagement between the main shaft 102 and the middle hollow rod 502 at the threaded section 504 can provide significant benefits, including but not limited to a self-locking against movement in a direction of the translational degree of freedom 104. Such locking is provided by the threaded engagement between the main shaft 102 and the middle hollow rod 502 at the threaded section 504 preventing externally urged linear movement of the main shaft 102 along the roll axis 105. The main shaft 102 can also be secured against forces and/or torques urging the main shaft 102 linearly in the linear direction of first rotational degree of freedom 106.

Figure 6A:
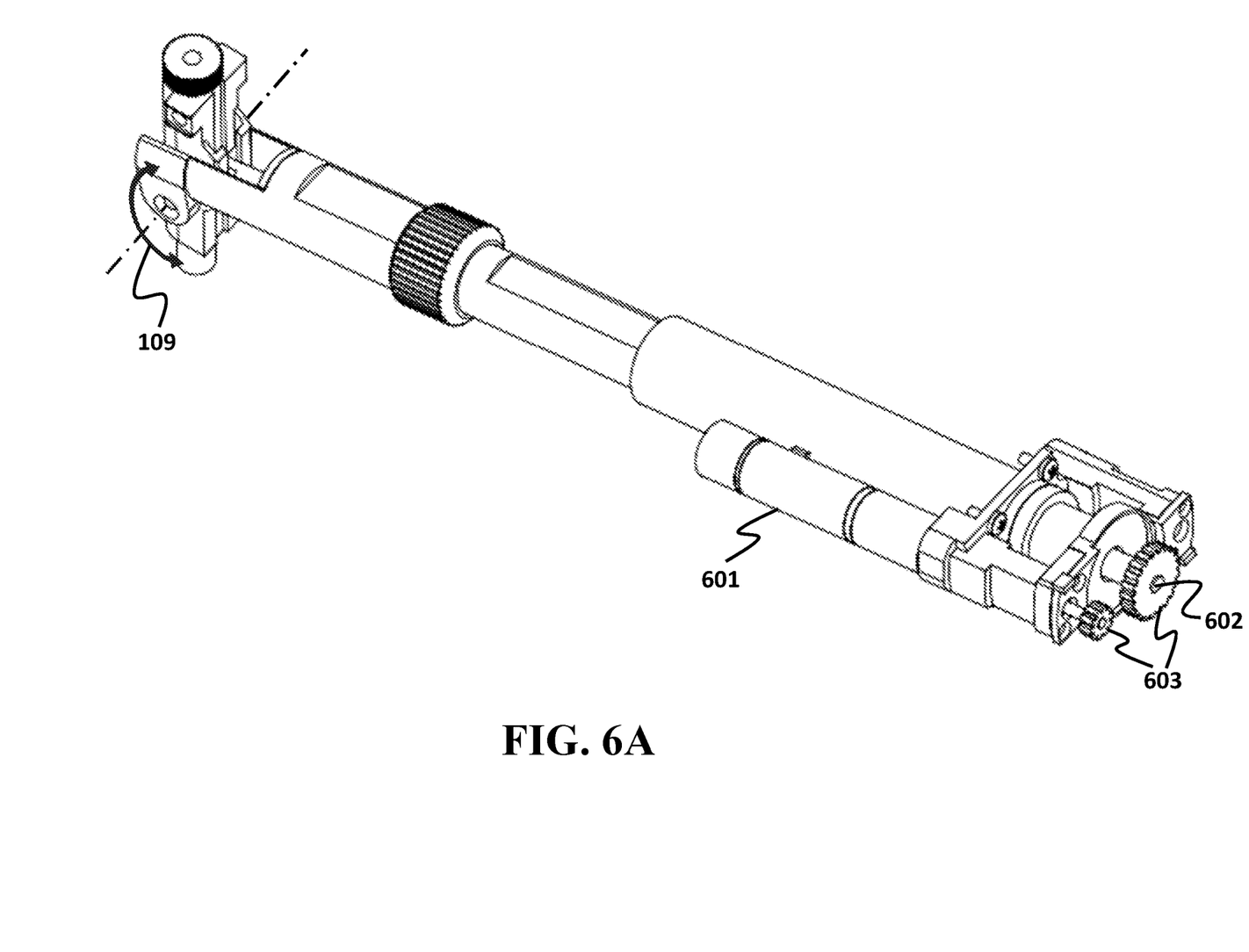
FIG. 6A illustrates a perspective view of an implementation of the robotic guide's components included in providing a pitch degree of freedom.
Figure 6B:
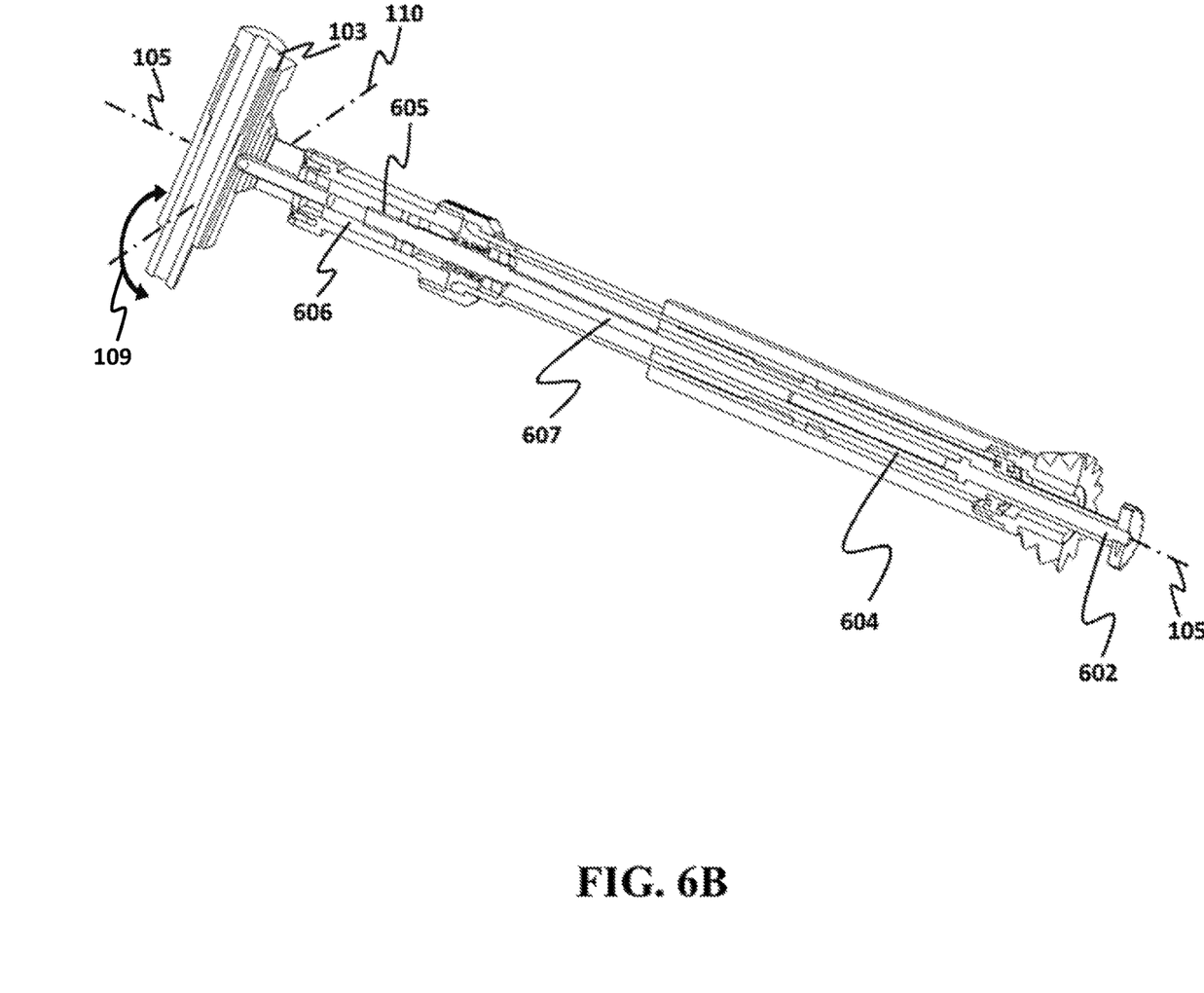
FIG. 6B illustrates a sectional detailed view of an implementation of the robotic guide's components included providing a pitch degree of freedom.

FIGS. 6A and 6B illustrate, graphically, an overview of various components and features of the robotic guide 100 respectively configured to operate together to provide the third rotational degree of freedom 109 for the robotic guide 100. FIG. 6B is a sectional view of the robotic guide 100, illustrating aspects according to one implementation of the present disclosure. Referring to FIG. 6A the disclosed robotic guide 100 can include a fourth motor 601 coupled to a first solid rod 602 via, for example, a fourth belt/pulley mechanism 603 (the belt of the fourth belt/pulley mechanism 603 is not shown in FIG. 6A). The pulley/belt mechanism 603 is only one example for coupling the fourth motor 601 to the first solid rod 602. Alternative implementations can couple the fourth motor 601 to the first solid rod 602 via other mechanisms, for example, a gear mechanism.

Referring to FIG. 6B, the first solid rod 602 can be tightly engaged with a hollow shaft 604 at a proximal end thereof and also a second solid rod 607 can be loosely engaged with the hollow shaft 604 at a distal end thereof. Using this arrangement, the rotation of the first solid rod 602 can urge a synchronous rotation of the hollow shaft 604 and the second solid rod 607 with the first solid rod 602. The loose engagement between the second solid rod 607 and the hollow shaft 604 can provide significant benefits including, but not limited to, allowing for free sliding of the second solid rod 607 inside the hollow shaft 604 without any surplus translational movement of the hollow shaft 604. In some implementations, a second threaded section 605 at the exterior surface of the second solid rod 607 may be provided to act as a screw, and a half-hollow rod 606, having an interior surface that is threaded, can be in a threaded engagement with the second solid rod 607 at the second threaded section 605. Due to this threaded engagement between the second solid rod 607 and the half-hollow rod 606 at the second threaded section 605, the half-hollow rod 606 can act as a nut for the second solid rod 607. Therefore, responsive to rotation of the second solid rod 607, the half-hollow rod 606 can move linearly in the direction of the roll axis 105. That movement can in turn urge rotation of the end-effector 103 about the pitch axis 110, through a slider-crank mechanism. This can provide the third rotational degree of freedom 109 for the end-effector 103 of the robotic guide 100.

The threaded engagement between the second solid rod 607 and the half-hollow rod 606 at the second threaded section 605 can provide significant benefits, including but not limited to a self-locking feature in the direction of the third rotational degree of freedom 109. The self-locking feature is provided by the threaded engagement between the second solid rod 607 and the half-hollow rod 606 at the second threaded section 605, as this prevents the externally-motivated linear movement of the half-hollow rod 606 along the roll axis 105. Therefore, the end-effector 103 may resist against forces and/or torques that, without such resistance, may cause the end-effector 103 to rotate in the direction of the third rotational degree of freedom 109.

Figure 7:
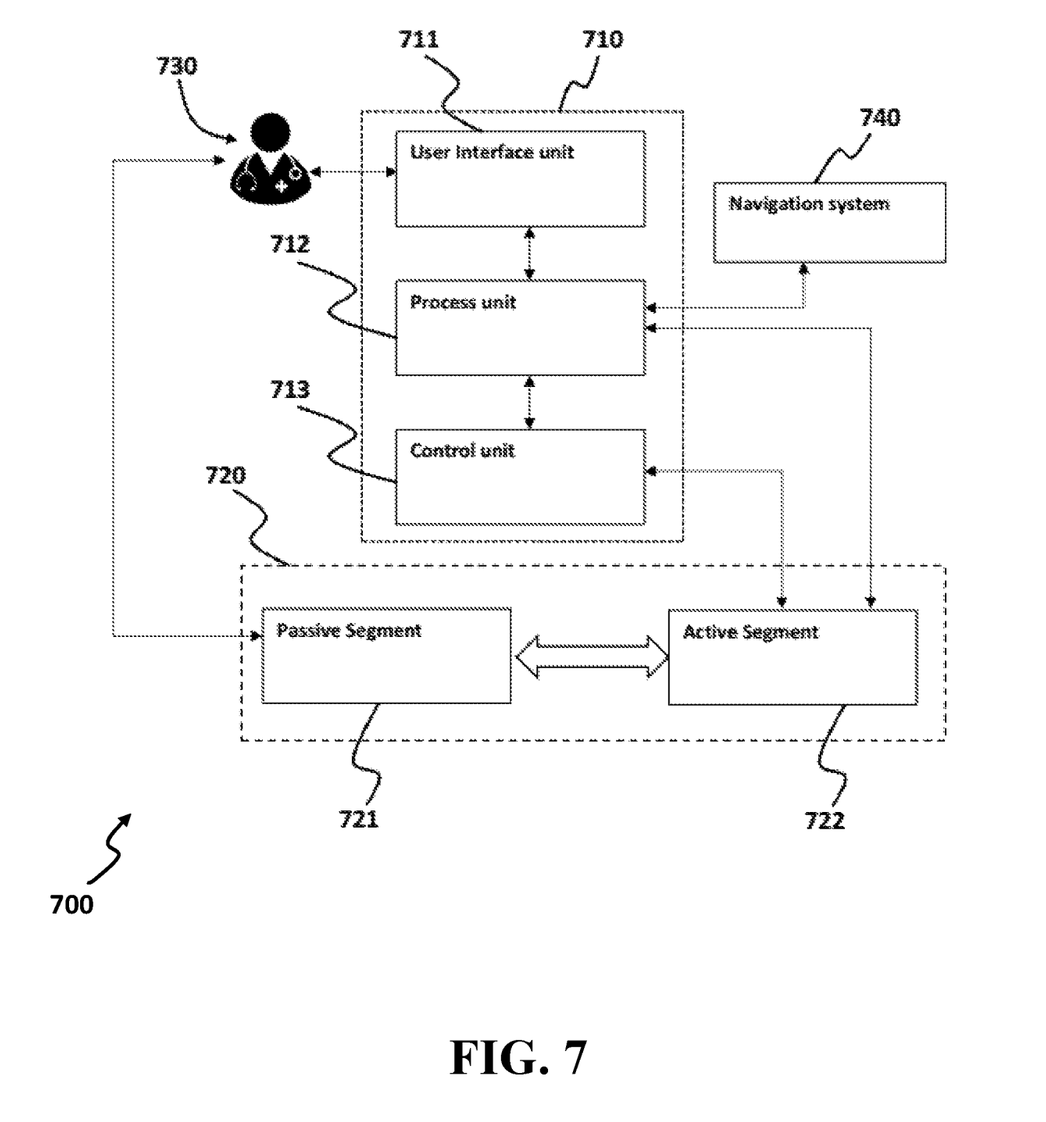
FIG. 7 illustrates a block diagram of one implementation of an example robotic surgical system.

FIG. 7 presents a block diagram of one implementation of an example robotic surgical system 700, directed to stereotactic biopsy according to one or more aspects of this disclosure. As shown in FIG. 7, the robotic surgical system 700 may include a software segment 710 and a hardware segment 720. In some implementations, the software segment 710 may include a user interface unit 711, a process unit 712 and a control unit 713. The user interface unit 711 may provide means for receiving data input from a surgeon 730. One implementation of the user interface unit 711 may include, for example, a graphical user interface (GUI) unit. The user interface unit 711 can provide means for the surgeon 730 to interactively control the motions of the robotic surgical system 700 for positioning and securing the robotic system's end-effector that may be understood to include substantially similar features as the end-effector 111 of the disclosed robotic guide 100. In some implementations, the process unit 712 may be responsible to process received input data from the user interface unit 711, received input data from a navigation system 740, and also received feedback data from active segment 722. In one implementation, the process unit 712 may send commands, based on the processed data, to a control unit 713. Furthermore, the control unit 713 may include a plurality of controllers configured to drive and control movements of the robot's axes. In some implementations, a respective controller may be coupled to each motor in order to control and drive movements of its associated motor's movements.

Furthermore, the hardware segment 720 may include a passive segment 721 and an active segment 722. The passive segment 721 of the robotic surgical system 700 may be configured to provide a number of passive DOFs to the robotic surgical system 700. Utilizing the passive DOFs of the passive segment 721 may facilitate the positioning of the robotic section in a work-space of the biopsy surgery near a patient's head by the surgeon 730. In other words, in some implementations, the passive segment 721 may be adjusted and/or controlled manually by the surgeon 730. It could be understood that the passive segment 721 of the surgical robotic system 700 may be mounted on any fixed rigid appliance present in a surgery room. For example, in one implementation, the passive segment 721 of the robotic surgical system 700 may be mounted on a Mayfield surgical table and/or a side rail of the surgical table.

According to some implementations, the active segment 722 may be a robotic guide that can include substantially similar features as the disclosed robotic guide 100 and is therefore able to provide 4 DOFs to the robotic surgical system. Further, in some implementations, the active segment of the robotic surgical system may include additional DOFs. For example, in one or more implementations, the active segment of the robotic surgical system can be configured for fine positioning of the end-effector of the robotic surgical system with respect to the target.

The disclosed system and device can allow a surgeon to accurately provide a path for biopsy needle through a minimally invasive procedure. DOFs of the disclosed robotic guide allow the surgeon to position and secure the end-effector thereof to the target accurately. The surgeon may provide a manual coarse positioning/securing for the robotic guide through the passive DOFs before implementation of the fine positioning through the active DOFs. The coarse positioning/securing through the passive segment can place the robotic guide in a position near to the target to make the robotic guide able to secure the end-effector thereof exactly to the target despite its limited range of operation. For purpose of reference, it can be understood upon reading this disclosure that some implementations of the robotic guide 100, for reasons including a desire for compactness, may have certain limits on ranges of one or more of the active DOFs. For example, referring back to FIG. 1, the first rotational degree of freedom 106 and the second rotational degree of freedom 107 may be configured to allow the rotation of the main shaft 102 about the roll axis

105 within a range, for example, between approximately −45° and approximately +45°. Similarly, rotation of the main shaft 102 about the yaw axis 108 can be limited within another range, for example, between −11° and +11°. It will be understood that the above examples of limits of the first rotational degree of freedom about the roll axis 105 and second rotational degree of freedom about the yaw axis 108 are only for examples, and are not intended as any limitation of ranges of the first or the second rotational degree of freedom in implementations according to aspects of this disclosure. In one or more implementations, the translational degree of freedom 104 may be configured to allow translational motion of the main shaft 102 in a range between, for example, 0 and 50 mm. In one or implementations, the third rotational degree of freedom 109 may be configured to allow the rotation of the end-effector 111 about the pitch axis 110 in a range between, for example, −40° and +40°. It will be understood that the above examples of limits of the translational degree of freedom 104 and of the third rotational degree of freedom 109 are only for examples, and are not intended as any limitation of such ranges in implementations according to aspects of this disclosure.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A robotic guide for a biopsy surgical tool, the robotic guide comprising:
 a main shaft, supported and rotatable about a main shaft axis;
 an end-effector, connected movably to a distal end of the main shaft in a configuration rotatable about a pitch axis;
 a roll/yaw actuating mechanism, comprising:
  a first actuating mechanism, including:
   a pinion mounted on a bottom of the main shaft,
   a bottom gear meshedly engaged with a bottom portion of the pinion, and rotatable about a yaw axis,
   a first motor, coupled though a first coupling to the bottom gear, the first coupling configured to convert rotation of the first motor to a rotation of the bottom gear,
  a second actuating mechanism, including:
   a top gear meshedly engaged with a top portion of the pinion,
   a second motor, coupled though a second coupling to the bottom gear, the second coupling configured to convert rotation of the second motor to a rotation of the top gear, wherein
   rotational movements of the first motor and the second motor convert to rotation of the top gear and the bottom gear in a similar direction to lock the pinion from rotating, and urge movement of the distal end of main shaft and the end effector in a yaw direction around the yaw axis, and wherein rotational movements of the first motor and the second motor that convert to rotation of the top gear and the bottom gear in mutually opposite directions rotate the main shaft about a roll axis, via the pinion;

a translational actuating mechanism, including:
a third motor;
a middle hollow rod, coupled to the third motor in a configuration wherein a rotation by the third motor urges a rotation of the middle hollow rod, the middle hollow rod including a first externally threaded section provided on an exterior surface thereof,
a first internally threaded section provided on an interior surface of the main shaft, the first internally threaded section being meshed with the first externally threaded section of the middle hollow rod such that a rotational movement of the middle hollow rod urges a linear movement of the main shaft; and a pitch actuating mechanism, including:
a slider-crank mechanism, provided with a crank end and movably supported by the main shaft for movement of crank end in a direction of the roll axis, the crank end being coupled to the end-effector in a configuration wherein movement of the crank end in the direction of the roll axis urges a pitch rotation of the end-effector.

2. The robotic guide of claim 1, wherein the bottom gear is a bottom reduced bevel gear, and the first coupling includes:
a first movement conversion mechanism, coupled to the first motor and to a first nut that is linearly movable along a first axis, the first coupling configured to convert a rotational movement of the first motor to the linear movement of the first nut, and
a first plurality of balls movably disposed within a first curved guiding path, the first nut engaging the first plurality of balls such that the linear movement of the first nut urges a movement of the first plurality of balls along the first curved guiding path, wherein:
the bottom reduced bevel gear includes two extended members at either ends thereof, engaged with the first plurality of balls in a configuration such that movement of the first plurality of balls along the first curved guiding path urges a rotation of the bottom reduced bevel gear about the yaw axis.

3. The robotic guide of claim 2, wherein the top gear is a top reduced bevel gear, and the second coupling includes:
a second movement conversion mechanism, coupled to the second motor and to a second nut that is linearly movable in a direction parallel the first axis, the second coupling to the second motor configured to convert a rotational movement of the second motor to the linear movement of the second nut, and
a second plurality of balls movably disposed within a second curved guiding path, the second nut engaging the second plurality of balls such that the linear movement of the second nut urges a movement of the second plurality of balls along the second curved guiding path, wherein:
the top reduced bevel gear includes two extended members at either ends thereof, engaged with the second plurality of balls in a configuration such that movement of the second plurality of balls along the second curved guiding path urges a rotation of the top reduced bevel gear about the yaw axis.

4. The robotic guide of claim 1, wherein the slider-crank mechanism includes:
a first solid rod, coupled to the fourth motor;
a first hollow shaft, coupled to the first solid rod such that the rotational movement of the first solid rod urges a synchronous rotation of the first hollow shaft;
a second solid rod including a second externally threaded section at a distal end thereof, the second solid rod being disposed slidably from a proximal end of the first hollow shaft, the second solid rod being coupled to the first hollow shaft such that the rotational movement of the first hollow shaft urges a synchronous rotation of the second solid rod; and
a half-hollow rod, the half-hollow rod including a second internally threaded section at a proximal end thereof, the second internally threaded section being meshed with the second externally threaded section such that the rotation of the second solid rod urges a linear movement of the half-hollow rod, wherein:
the end-effector is connected through a pin to a distal end of the half-hollow rod, and
the linear motion of the half-hollow rod urges, through the pin, a tilting of the end-effector with respect to the longitudinal axis of the main shaft.

5. The robotic guide of claim 1, wherein the first motor, second motor, first coupling, second coupling, bottom gear and top gear are configured such that rotational movements of the first motor and the second motor that convert to rotation of the top gear and the bottom gear in similar directions and unequal speeds urges rotation of the main shaft about the roll axis, via the pinion, simultaneous with urging movement of the main shaft that moves its distal end and the end effector in the yaw direction around the yaw axis.

6. A robotic guide for a biopsy surgical tool, the robotic guide comprising:
a main shaft;
an end-effector mounted on a distal end of the main shaft;
a roll/yaw actuating mechanism, including:
a first actuating mechanism that includes:
a first motor,
a first screw/nut mechanism including a first nut mounted on a first screw coupled to the first motor, the first screw/nut mechanism being configured to convert a rotational movement of the first motor to a linear movement of the first nut along a first axis;
a first plurality of balls movably disposed within a first curved guiding path, the first nut engaging the first plurality of balls such that the linear movement of the first nut along the first axis urges a movement of the first plurality of balls along the first curved guiding path,
a bottom reduced bevel gear including two extended parts at either ends thereof, wherein the two extended parts are engaged with the first plurality of balls in a configuration wherein the movement of the first plurality of balls along the first curved guiding path urges the linear movement of the first nut along the first axis to a rotational movement of the bottom reduced bevel gear around a central axis of the bottom reduced bevel gear;

a second actuating mechanism, including:
   a second motor,
   a second screw/nut mechanism including a second nut mounted on a second screw, the second screw being coupled to the second motor, the second screw/nut mechanism configured to convert a rotational movement of the second motor to a linear movement of the second nut along the first axis,
   a second plurality of balls movably disposed within a second curved guiding path, the second nut engaging the second plurality of balls such that the linear movement of the second nut along the second axis urges the movement of the second plurality of balls along the second curved guiding path,
   a top reduced bevel gear including two extended parts at either ends thereof, the two extended parts being engaged with the second plurality of balls, in a configuration wherein the movement of the second plurality of balls along the second curved guiding path converts the linear movement of the second nut along the first axis to a rotational movement of the top reduced bevel gear around a central axis of the top reduced bevel gear,
wherein:
   the bottom reduced bevel gear couples to the main shaft via a meshing with a bottom perimeter of a pinion mounted on the main shaft from the bottom, and
   the top reduced bevel gear couples to the main shaft via a meshing with a top perimeter of the pinion, and wherein:
   responsive to rotational movements of the first motor and the second motor in a similar direction, the respective meshing of the top reduced bevel gear and the bottom reduced bevel gear to the pinion urges an arcuate rotation of the distal end of the main shaft about a central axis, and
   responsive to rotational movements of the first motor and the second motor in opposite direction, the respective meshing of the top reduced bevel gear and the bottom reduced bevel gear to the pinion urges a rolling of the main shaft about a longitudinal axis that is orthogonal to the central axis;
a translational actuating mechanism, including:
   a third motor,
   a middle hollow rod, coupled to the third motor, the middle hollow rod including a first externally threaded section provided on an exterior surface thereof,
   a first internally threaded section provided on an interior surface of the main shaft, the internally threaded section being meshed with the externally threaded section such that the rotational movement of the middle hollow rod urges a linear movement of the main shaft; and
a pitch actuating mechanism, including:
   a fourth motor,
   a first solid rod, coupled to the fourth motor,
   a first hollow shaft, coupled to the first solid rod in a configuration wherein the rotational movement of the first solid rod urges a synchronous rotation of the first hollow shaft,
   a second solid rod including a second externally threaded section at distal end thereof, the second solid rod being disposed slidably from a proximal end thereof in the first hollow shaft, the second solid rod being coupled to the first hollow shaft in a configuration wherein the rotational movement of the first hollow shaft urges a synchronous rotation of the second solid rod,
   a half-hollow rod, the half-hollow rod including a second internally threaded section at a proximal end thereof, the second internally threaded section being meshed with the second externally threaded section in a configuration wherein the rotation of the second solid rod urges a linear movement of the half-hollow rod,
wherein:
   the end-effector is mounted on the distal end of the main shaft in a configuration such that the end-effector moves/rotates synchronously with the main shaft during yaw motion, roll motion and translational motion of the main shaft,
   the end-effector is connected with a pin to a distal end of the half-hollow rod, in a configuration wherein, responsive to the linear movement of the half-hollow rod, the end-effector tilts about the longitudinal axis of the main shaft through a slider-crank mechanism.

7. A robotic guide for a biopsy surgical tool, the robotic guide comprising:
a main shaft;
an end-effector mounted on a distal end of the main shaft;
a roll/yaw actuating mechanism, comprising:
   a first actuating mechanism, including:
      a first motor,
      a first screw/nut mechanism including a first nut mounted on a first screw, the first screw coupled to the first motor, the first screw/nut mechanism configured to convert a rotational movement of the first motor to a linear movement of the first nut along a first axis,
      a first plurality of balls movably disposed within a first curved guiding path, the first nut engaging the first plurality of balls such that the linear movement of the first nut along the first axis causing the movement of the first plurality of balls along the first curved guiding path, and
      a bottom reduced bevel gear including two extended parts at either ends thereof, the two extended parts engaged with the first plurality of balls, the movement of the first plurality of balls along the first curved guiding path converting the linear movement of the first nut along the first axis to rotational movement of the bottom reduced bevel gear around a central axis of the bottom reduced bevel gear;
   a second actuating mechanism, including:
      a second motor,
      a second screw/nut mechanism including a second nut mounted on a second screw, the second screw coupled to the second motor, the second screw/nut mechanism configured to convert a rotational movement of the second motor to a linear movement of the second nut along the first axis,
      a second plurality of balls movably disposed within a second curved guiding path, the second nut engaging the second plurality of balls such that the linear movement of the second nut along the second axis causing the movement of the second plurality of balls along the second curved guiding path, and a top reduced bevel gear including two extended parts at either ends thereof, the two extended parts engaged with the second plurality of balls, the movement of the second plurality of balls along the second curved guiding path converting the linear movement of the second nut along the first axis to rotational movement of the top reduced bevel gear around a central axis of the top reduced bevel gear, wherein,
the bottom reduced bevel gear is coupled to the main shaft via meshing with a pinion mounted on the main shaft from the bottom, and the top reduced bevel gear is coupled to the main shaft via meshing with the pinion mounted on the main shaft from the top, wherein:

responsive to rotational movements of the first motor and the second motor in a similar direction, the main shaft rotates about the central axis, and responsive to rotational movements of the first motor and the second motor in opposite directions, the main shaft rolls about a longitudinal axis of the main shaft.

8. The robotic guide of claim 7, further comprising:
a translational actuating mechanism including:
  a third motor;
  a middle hollow rod; the middle hollow rod coupled to the third motor, the middle hollow rod including a first externally threaded section provided on an exterior surface thereof,
  a first internally threaded section provided on an interior surface of the main shaft, the internally threaded section meshed with the externally threaded section such that the rotational movement of the middle hollow rod causing the linear movement of the main shaft.

9. The robotic guide of claim 8, further comprising:
a pitch actuating mechanism including:
  a fourth motor;
  a first solid rod; the first solid rod coupled to the fourth motor,
  a first hollow shaft, coupled to the first solid rod such that the rotational movement of the first solid rod urges a synchronous rotation of the first hollow shaft,
  a second solid rod including a second externally threaded section at distal end thereof, the second solid rod disposed slidably from proximal end thereof in the first hollow shaft, the second solid rod coupled to the first hollow shaft in a configuration wherein the rotational movement of the first hollow shaft urges a synchronous rotation of the second solid rod,
  a half-hollow rod, the half-hollow rod including a second internally threaded section at a proximal end thereof, the second internally threaded section being meshed with the second externally threaded section such that the rotation of the second solid rod urges the linear movement of the half-hollow rod,
  the end-effector including a passage, the end-effector mounted on a distal end of the main shaft such that the end-effector moves/rotates synchronously with the main shaft during yaw motion, roll motion and translational motion of the main shaft, wherein
  the end-effector is connected with a pin to a distal end of the half-hollow rod, and wherein,
  responsive to the linear motion of the half-hollow rod, the end-effector tilts about the longitudinal axis of the main shaft through a slider-crank mechanism.

* * * * *